United States Patent [19]

Vandeberg

[11] 4,402,210
[45] Sep. 6, 1983

[54] ACOUSTIC SIGNATURE INSPECTION OF RAILROAD WHEELS

[76] Inventor: Robert M. Vandeberg, 5622 S. 139th St., Omaha, Nebr. 68137

[21] Appl. No.: 303,198

[22] Filed: Sep. 17, 1981

[51] Int. Cl.³ .................... G01N 3/30; G01N 29/04
[52] U.S. Cl. .......................................... 73/12; 73/662
[58] Field of Search .................................. 73/12, 662

[56] References Cited

U.S. PATENT DOCUMENTS

| | | | |
|---|---|---|---|
| 2,418,437 | 4/1947 | Vogt | 73/12 |
| 2,422,317 | 6/1947 | Stock et al. | 73/12 |
| 2,721,971 | 10/1955 | Francois | 73/12 |
| 3,557,603 | 1/1971 | Carr | 73/12 |

*Primary Examiner*—Anthony V. Ciarlante
*Attorney, Agent, or Firm*—Robert A. Ostmann

[57] ABSTRACT

The disclosure concerns an electromagnetic exciter for striking the wheels of moving railroad cars undergoing acoustic signature inspection. The apparatus comprises a pivotally mounted impact member which is accelerated by a solenoid through only a portion of its impact stroke and then moves onward to impact solely as a result of the kinetic energy imparted to it during the initial acceleration period. The solenoid is controlled by an electronic drive circuit which responds to an input signal from a wheel presence detector and delivers to the solenoid coil a burst of energy whose size and duration may be adjusted to yield the greatest sound pressure level while allowing the field of the coil to relax quickly enough to reset the apparatus for the next car wheel.

9 Claims, 5 Drawing Figures

ACOUSTIC SIGNATURE INSPECTION OF RAILROAD WHEELS

BACKGROUND AND SUMMARY OF THE INVENTION

This invention concerns exciter apparatus for use in acoustic signature inspection of railroad car wheels.

Acoustic signature inspection provides an automated technique for detecting cracked wheels on moving railroad cars. This technique involves use of a trackside exciter which strikes a passing wheel to produce a sound pressure level which is significantly greater than ambient noise, and a spectrum analyzer which interprets the resulting sound spectrum of the impacted wheel. Data from the analyzer is read by a digital computer, which compares it with corresponding information obtained from the similarly excited opposite wheel on the same axle, and then makes a wheel evaluation using the assumption that the spectra of two good wheels on a common axle will be the same. Fuller discussions of the complete inspection process are contained in the following reports:

"Operational Parameters In Acoustic Signature Inspection of Railroad Wheels, D. Dousis and R. D. Finch, University of Houston, Final Report October, 1978 (prepared for U.S. Department of Transportation under Contract DOT-TSC-1187).

"Test Report For The Cracked Plate Detector Tests (Series 1) At The Transportation Test Center, November, 1980 (prepared by University of Houston under Subcontract No. W-0276 to The Aerospace Corporation for U.S. Department of Transportation, Contract No. FO 4701-C-0078).

The exciter employed in an acoustic inspection system must be capable of producing the required sound pressure level in a train speed range of about 2-15 MPH, and the resulting sound signature must be reproducible and independent of train speed. In addition, the exciter must be suitable for use outdoors at virtually any location, present no hazard to the train, satisfy normal railroad requirements for trackside apparatus, including personnel safety requirements, and be sufficiently durable to have a reasonable useful life. As indicated in the reports mentioned earlier, various exciters prior to mine were considered and/or evaluated and found unacceptable.

The object of the present invention is to provide an improved form of exciter which satisfies fully the requirements of a practical acoustic signature inspection system. According to the invention, the new exciter takes the form of an electromagnetic hammer, the mechanical portion of which comprises a pivotally mounted impact member which is actuated by a solenoid through a special lost motion connection. That connection is designed so that the solenoid moves the impact member through only an initial phase of its impact stroke, thereby imparting to the member sufficient kinetic energy to carry it through the balance of that stroke and into contact with the passing wheel. The solenoid is controlled by an electronic drive circuit which responds to an input signal from a wheel presence detector and delivers to the solenoid coil a burst of electrical energy whose magnitude and duration are selected, and preferably adjustable, to yield the maximum sound pressure level from the impact. The circuit enables the magnetic field of the coil to relax quickly so that the apparatus will reset in the short time interval between passage of successive wheels, even at relatively high train speeds.

The magnitude of the impact produced by the new exciter is independent of train speed. Moreover, since the impact member is not coupled rigidly to the solenoid armature throughout the stroke, but has a range of free motion, the mechanical and electrical portions of the apparatus may be field tuned spearately for optimum performance. As a result, the apparatus can operate and produce a relatively uniform and sufficiently great sound pressure level at any train speed within the range of about 2-15 MPH.

BRIEF DESCRIPTION OF THE DRAWINGS

The preferred embodiment of the invention is described herein with reference to the accompanying drawings, in which.

DETAILED DESCRIPTION OF ILLUSTRATED EMBODIMENT

Figure 1:
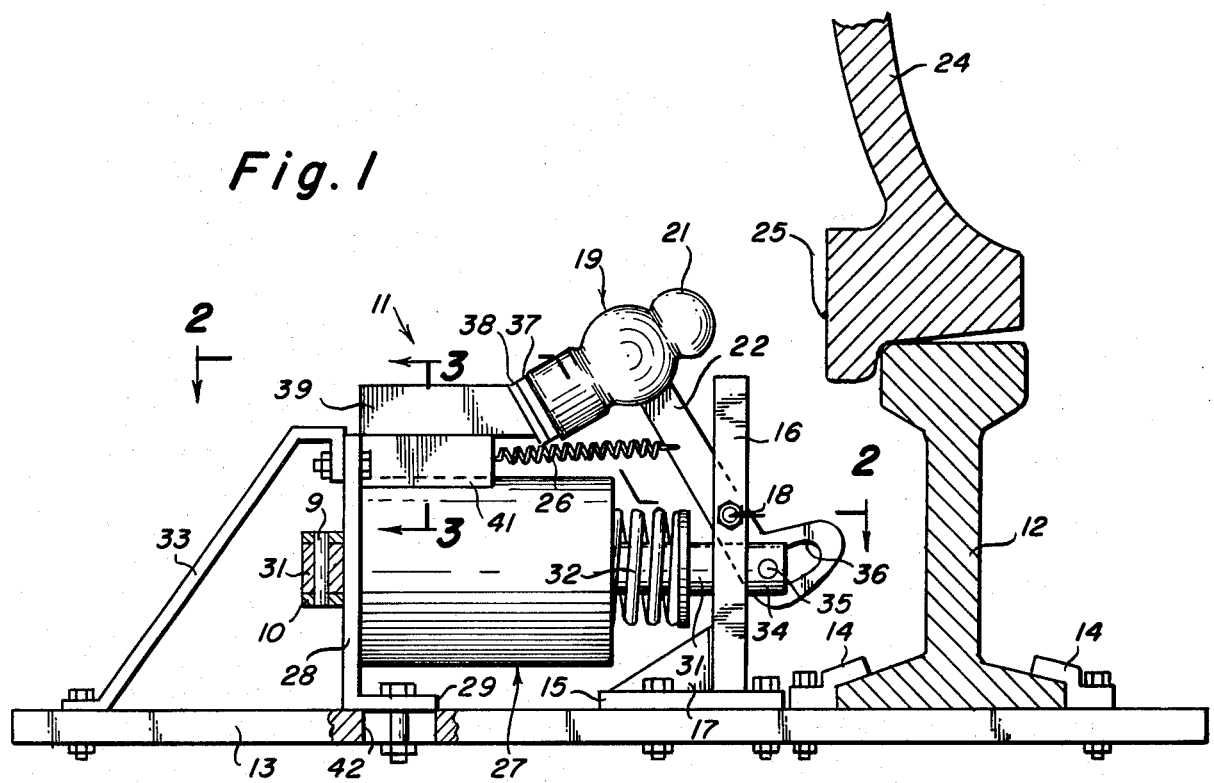
FIG. 1 is a side elevation view of the mechanical portion of the exciter, showing the unit in place on a track.
Figure 2:
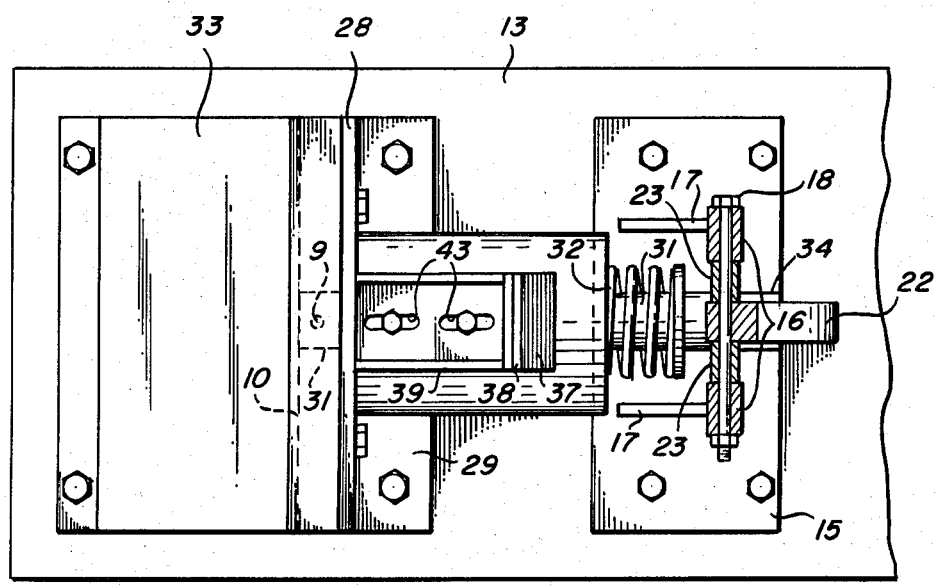
FIGS. 2 and 3 are sectional views taken on lines 2—2 and 3—3, respectively, of FIG. 1.
Figure 3:
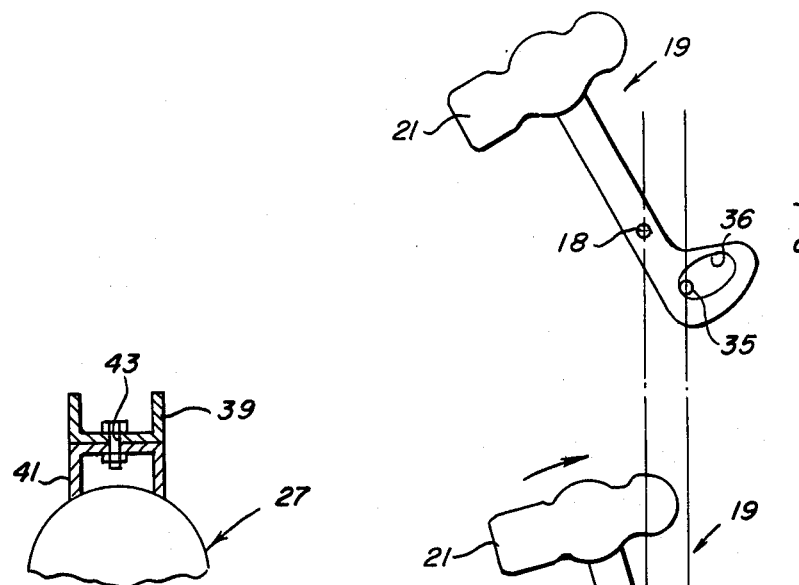

Referring to FIGS. 1-3, the improved exciter comprises a mechanical striking unit 11 which is designed to be mounted between the ties of a roadbed adjacent the inboard or gage side of a rail 12. Unit 11 includes a steel base plate 13 which underlies rail 12 and is attached to the rail base by a pair of clamps 14. Base Plate 13 carries a support assembly comprising a flat steel mounting plate 15 which is bolted to the base and to which are welded a pair of columns 16 and a pair of reinforcing gusset plates 17. The columns are drilled to receive a bolt 18, which serves as a pivot for a swinging impact member 19. This member comprises a striking head 21, which conveniently is a 15 ounce ball pein hammer head of the kind commonly found in railroad shops, and a steel pivot arm 22 which is journaled on bolt 18 and is centered by a pair of spacers 23. The pivot axis for impact member 19 is horizontal and parallel with rail 12, and the parts are dimensioned and arranged so that striking head 21 will strike a passing wheel 24 at a point 25 low down on the wheel rim.

Impact member 19 is biased by a coil tension spring 26 to the illustrated inactive position, defined by a cushioned stop described later, and is swung from this position on its impact stroke by a solenoid 27. The solenoid, which preferably is an AC MFG. 14-183-021 unit commonly employed in the switch gear of railroad locomotives, comprises a casing which houses the coil and is equipped with a flange 28 having a mounting foot 29, a reciprocable armature 31, and a return spring 32. The commercial form of solenoid 27 also includes a U-shaped return stop, the uprights of which are not used here and can be removed to yield a bar shaped stop 10. This stop 10 is connected to the left end of armature 31 by a roll pin 9, and thus determines the return stroke limit of the armature. Solenoid 27 is attached to base plate 13 by bolts which pass through foot 29, and by a reinforcing steel bracket 33 which is bolted to plate 13 and flange 28.

The free end of solenoid armature 31 is provided with a clevis 34 which receives the lower end of pivot arm 22, and these parts are connected by a lost motion connection comprising a pin 35 carried by the clevis and which passes through an oval slot 36 formed in the pivot arm. This connection is so designed that the solenoid swings impact member 19 through only about one-half of its impact stroke, and thereafter allows that member to move into impact with a passing wheel 24 solely as a result of the kinetic energy imparted to it during the initial stage of the stroke. The arrangement allows separate adjustment of the response characteristics of the mechanical and electrical portions of the apparatus thereby enabling the exciter to operate satisfactorily over a wider range of train speeds than overwise would be possible.

The inactive position of impact member 19 illustrated in FIG. 1 is defined by a stop comprising a rubber pad 37 bonded to a steel plate 38 welded across one end of a channel member 39. This member 39, in turn, is bolted back-to-back to a support channel 41 which is welded in place on the top of the casing of solenoid 27 and, incidentally, also services as an anchor for one end of return spring 26. Since the car wheels 24 have a much greater mass than impact member 19, the latter rebounds rapidly from impact with a wheel, and thus tends to bounce or rebound when it returns to inactive position. This tendency must be suppressed, so that the apparatus will reset rapidly and be ready to strike the next wheel, and this function is performed by pad 37. Experience indicates that a pad $\frac{3}{8}''$ to $\frac{1}{2}''$ thick affords adequate damping or shock-absorbing action for the reset rates needed to accommodate train speeds up to 15 MPH.

It will be observed that, as indicated in FIGS. 1 and 2, the holes 42 in base 13 which receive the mounting bolts for plate 15, foot 29 and bracket 33, and the mounting holes 43 for the attaching bolts of channel 39 all are elongated in directions parallel with the plane of swing of impact member 19. Such holes, of course, afford adjustability to the connected parts. This is desirable, first, because it allows the position of the assemply 15, 16 and 19 relative to wheel 24 to be adjusted so that the blow delivered by head 21 is directed horizontally, and thus has the greatest sound-producing effect. After the assemply including impact member 19 has been properly positioned, the position of solenoid 27 and stop 37 may then be adjusted to afford to head 21 the required length of impact stroke, and to bring pin 35 into contact with the coacting end of slot 36. These last mentioned adjustments also may be made following replacement of a worn pad 37, thereby preserving the operational characteristics of unit 11.

Figure 4:
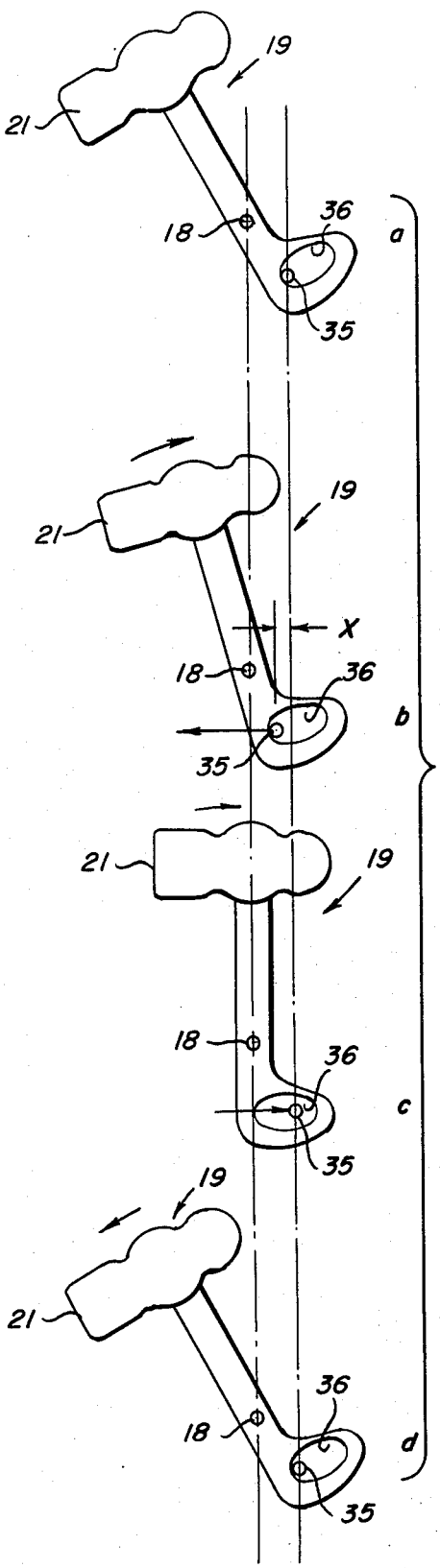
FIG. 4 is a series of four diagrams showing various stages in a cycle of the impact member.

Various stages in a cycle of impact member 19 are illustrated in the diagrams of FIG. 4. Stage a shows the initial conditions, wherein impact member 19 is in its inactive position, the solenoid 27 is deenergized, and pin 35 rests against the left end of slot 36. As a car wheel approaches, the solenoid is energized, thereby retracting armature 31 and causing pin 35 to move to the left through the distance X shown in diagram b. This motion of pin 35, swings impact member 19 in the clockwise direction about pivot 18 and brings head 21 to a position in approximately the middle of its impact stroke. The kinetic energy imparted to impact member 19 in the interval between stages a and b carries that member onward to the wheel impact position represented in diagram c. In this interval, solenoid 27 is deenergized, so return spring 32 moves armature 31 to its extended position, and thus, shifts pin 35 back to its initial position. Since, in this stage, pin 35 is positioned between the opposite ends of slot 36, the motion of impact 19 is not influenced by the dynamic response of the solenoid. After impact, member 19 swings in the counterclockwise direction, as indicated in diagram d and returns to its inactive position under the combined effect of rebound and the biasing force of spring 26. The momentum of the impact member is absorbed by antirebound pad 37, so member 19 comes to a rest upon reaching the inactive position, and the left end of slot 36 again is brought into contact with pin 35. The apparatus, therefore, is now ready to strike the following wheel on the same side of the train.

It might be well to remark here that a complete acoustic signature inspection system includes a pair of exciter units 11, one located adjacent the gage side of each rail, and that these units are activated alternately so that both wheels on an axle will be struck before the next succeeding axle reaches the inspection station.

Proper functioning of the mechanical unit 11 requires that solenoid 27 be supplied with a burst of electrical energy sufficient to enable impact member 19 to produce the required sound pressure level, and that the magnetic field of the solenoid relax rapidly enough to accommodate the reset rate required for the apparatus. It also is preferred that both the duration and the size of said energizing burst be adjustable in the field. These purposes are fulfilled by the electronic drive circuit now to be described.

Figure 5:
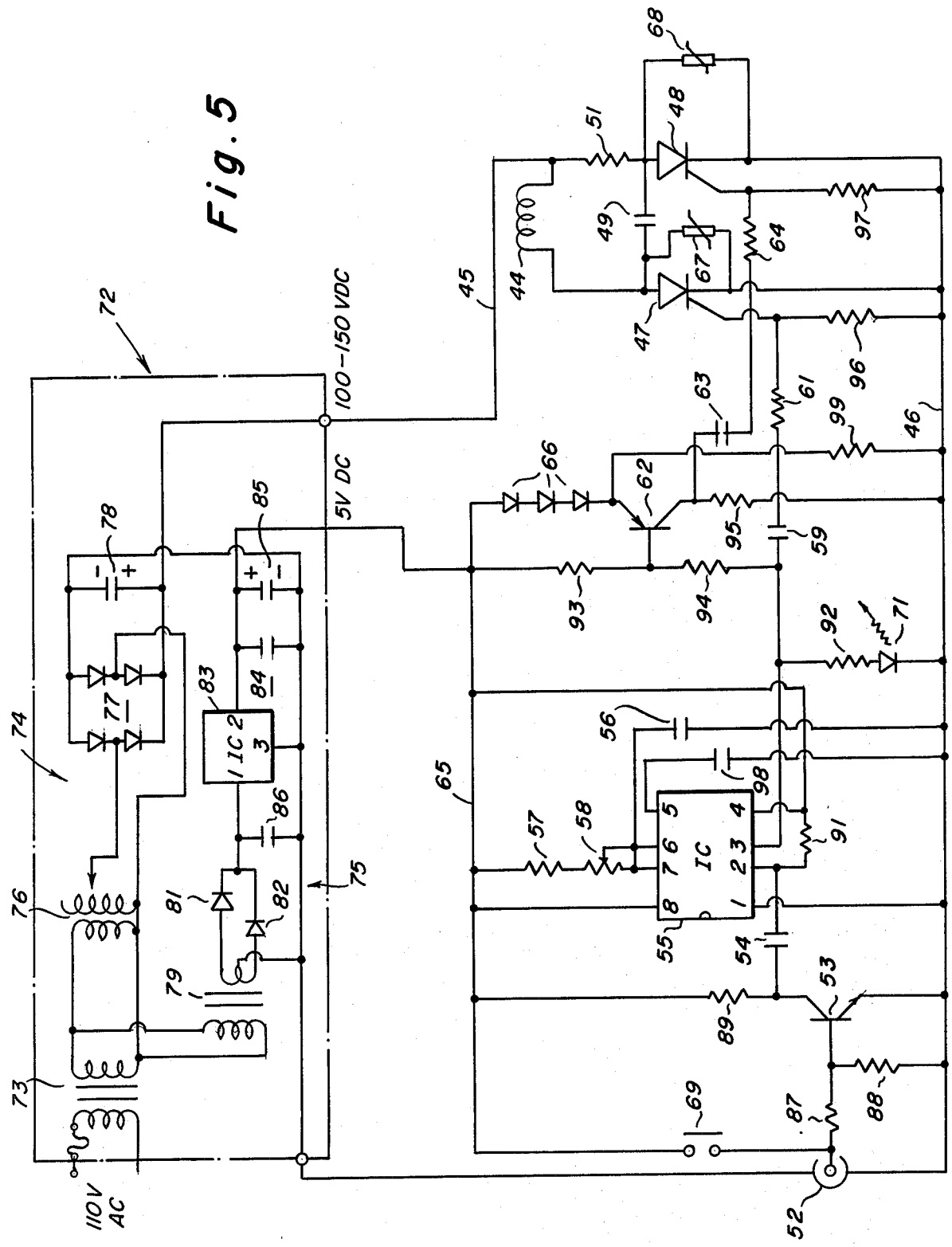
FIG. 5 is an electrical schematic of the electronic drive circuit.

As shown in FIG. 5, the coil 44 of solenoid 27 is connected in a power circuit including input lead 45, common return lead 46, and a pair of controlled rectifiers (hereafter termed SCRs) 47 and 48. The anodes of SCRs 47 and 48 are connected with opposite ends of coil 44, so SCR 47 is in series with the coil and SCR 48 is in a shunt or parallel path. Connected between the anodes of the SCRs is a capacitor 49, which is charged in one direction through coil 44 when SCR 48 conducts, and is charged in the opposite direction through a low value, high wattage resistor 51 when SCR 47 conducts. As will be explained later, the charges developed on capacitor 49 serve to reverse the direction of current flow through whichever SCR controls charging when the other SCR becomes conductive. This action, in conjunction with the polarities of the pulses supplied to the SCR gates, causes the SCRs to conduct alternately.

The electronic drive circuit responds to an imput signal which is delivered to jack 52 from a wheel presence detector (not shown). Introduction of this signal is so timed that impact member 19 will strike each passing wheel at a point near, but spaced from, the veritcal center plane of the axle, because it has been found that this arrangement yields the greatest sound pressure level. The input signal is coupled through transistor 53 and capacitor 54 to an IC timing chip 55, which is connected to operate as a monostable multivibrator. In response to the input, IC 55 produces a positive control pulse whose duration is dependent upon the values of capacitor 56, resistor 57 and potentiometer 58, and which is coupled directly from pin 3 of IC 55 to the gate of SCR 47 through capacitor 59 and resistor 61. The control pulse also is coupled indirectly to the gate of SCR 48 via transistor 62, capacitor 63 and resistor 64. This coupling path serves as an inverter. Therefore, at the commencement of the control pulse (i.e., when the output voltage of IC 55 rises), the gate of SCR 47 receives a positive pulse, which renders that SCR conductive, and the gate of SCR 48 receives a negative pulse, which enables that SCR to turn off under the action of discharging capacitor 49. On the other hand, at the end of the control pulse (i.e., when the output voltage at pin 3 of IC 55 returns to its normal low level), the polarities of the pulses applied to the SCR gates reverses, thereby causing SCR 48 to become conductive and enabling SCR 47 to turn off. Coil 44 is, of course, energized during the time period in which SCR 47 conducts, and that period can be adjusted by changing the setting of potentiometer 58. The particular setting used is a compromise between the conflicting demands of achieving the greatest sound pressure level while insuring that the apparatus will reset fast enough to accommodate train speeds at the upper limit of the desired speed range.

As a result of internal losses, the control pulse produced by IC 55 may be 1-2 volts less than the voltage at low voltage supply lead 65. Since reliable cut-off of transistor 62 requires that the emitter voltage be less than the base voltage, the connection between the emitter and supply lead 65 must produce a voltage drop somewhat larger than that attributable to the internal losses in IC 55. This voltage-dropping function is performed by a set of three similar diodes 66 and a resistor 99. The voltage dropping effect of the diodes also offsets the adverse effect of temperature changes on the characteristics of transistor 62.

As indicated earlier, it is important, from the standpoint of rapid resetting of the exciter, that the magnetic field of coil 44 relax quickly. Therefore, the coil circuit is free of any damping or arc-suppressing diodes. However, since the large voltage spikes which could result from this arrangement may damage SCRs 47 and 48, the drive circuit must include some protective measure. In the illustrated circuit, such protection is afforded by a pair of voltage dependent resistors (VDRs) 67 and 68, each of which is connected between the anode and cathode of one SCR and serves to freely by-pass current around the SCR when the impressed voltage reaches a level above the normal operating voltage, but safely below the damaging level. An acceptable level is about 180 volts for the illustrated circuit, wherein normal operating voltage is in the range of 100-150 volts.

The preferred drive circuit includes a manually operated switch 69, which is connected to provide a simulated input signal and is used for initial tuning of the electrical and mechanical portions of the exciter. It is also convenient to include a light-emitting diode 71 which responds to the control pulses produced by IC 55 and provides a visual indication that the integrated circuit is operating properly.

It is also preferred that the drive circuit include its own power supply 72 for producing the needed high and low DC voltages. This power supply includes an isolation transformer 73 and separate high and low voltage sections 74 and 75, respectively. High voltage section 74 comprises an autotransformer 76, a diode bridge rectifier 77 and a filter capacitor 78. This section is designed to deliver to power lead 45 a supply voltage in the range of 100-150 volts, depending upon the setting of the tap of transformer 76. The capability of adjusting the output of high voltage section 74 is an advantageous feature because it allows field tuning of the exciter for optimum performance.

Low voltage power supply section 75 comprises a fullwave rectifier in the form of a center tapped transformer 79 and a pair of diodes 81 and 82, a voltage regulating IC chip 83, and a pair of output filter capacitors 84 and 85. Ripple in the input to IC 83 should be minimized, so the circuit also incorporates an input filter capacitor 86. Section 75 is desired to deliver to lead 65 a constant 5 volts.

The specific components employed in one acceptable embodiment of the illustrated drive circuit are listed in the Appendix.

When the drive circuit is in service, SCRs 47 and 48 normally will be in the non-conducting and conducting states respectively. Therefore, the current delivered to lead 45 by high voltage power section 74 is by-passed around coil 44 through SCR 48, and the coil is de-energized. Since, at this time, the right side of capacitor 49 will be at essentially ground potential, this capacitor will be charged through coil 44 to the level required to perform its intended SCR turn-off function.

As a wheel approaches the exciter station, an input signal is generated by a wheel presence detector and applied to jack 52. This signal turns on transistor 53 and thereby causes an input voltage spike to be applied to IC 55 through cpacitor 54. This input triggers the production of a positive control pulse at pin 3 of IC 55. As the output voltage of IC 55 rises, the gate of SCR 47 receives a positive turn on pulse through capacitor 59, and this SCR becomes conductive. Simultaneously, the control pulse turns off transistor 62 and causes a negative pulse to be applied to the gate of SCR 48. The change of state of SCR 47 drops the voltage at the left side of capacitor 49 to essentially ground potential, so the capacitor discharges and effectively reverses the direction of current flow through SCR 48. Since, at this instant, the gate of SCR 48 is receiving a negative pulse, that SCR turns off and opens the shunt path around coil 44. As a result, the electrical power supplied by section 74 is conveyed through coil 44 and SCR 47, and the coil energizes and swings impact member 19 on its impact stroke. In addition, capacitor 49 now commences to charge through resistor 51. The values of capacitor and resistor 51 are so chosen that the capacitor will charge to the level needed for the subsequent SCR turn off function in a time period equal to or less than the duration of the control pulse produced by IC 55.

The contal pulse produced by IC 55 has a predetermined duration selected by adjustment of potentiometer 58 to give the best overall performance of the exciter, keeping in mind the conflicting requirements for a high sound pressure level and a short reset time. At the end of that pulse, when IC output voltage returns to a low level a negative voltage spike is applied to the gate of SCR 47 through capacitor 59, thereby enabling, but not directly causing, that SCR to turn off. At the same time, the falling edge of the control pulse turns on transistor 62 and causes a positive gating pulse to be delivered to the gate of SCR 48 through capacitor 63. As a result, SCR 48 becomes conductive, the voltage at the right side of capacitor 49 drops to essentially ground potential, and that capacitor discharges and effects a reversal in the direction of current flow through SCR 47. Since SCR 47 has been enabled to turn off by the application of a negative pulse to its gate, that SCR now becomes non-conductive. Accordingly, the power supplied by section 74 is diverted around coil 44 through SCR 48, the coil is de-energized, and capacitor 49 again charges through the alternative path containing the coil. The circuit components remain in this condition until another input signal is delivered to jack 52.

APPENDIX

| COMPONENTS | VALUES OR TYPES |
|---|---|
| Resistors (¼ watt, except where noted-resistance in ohms) | |
| 51 (50 watt) | 750 |
| 57, 87, 89, 91 and 99 | 10K |
| 58 | 50K |
| 61 and 95 | 270 |
| 64 | 100 |
| 88 and 93 | 47K |
| 92 | 470 |
| 94 | 4.7K |
| 96 and 97 | 1K |
| Capacitors (capacitance in microfarads) | |
| 49 | 4 |
| 54 and 84 | 0.1 |
| 56 | 1 |
| 59, 63 and 86 | 100 |
| 78 and 85 | 500 |
| 98 | 0.05 |
| Transformers | |
| 73 | TRIAD N-53MG |
| 76 | STACO 171 |
| 79 | THORD. 21F174 |
| Miscellaneous | |
| SCR 47 and 48 | C35D |
| Transistor 53 | 2N3904 |
| Transistor 62 | 2N3906 |
| IC 55 | LM 555 |
| IC 83 | LM 309K |
| Diodes 66 | IN 914 |
| Diodes 77, 81 and 82 | ECG-125 |
| VDR 67 and 68 | VR 180 AZ |

I claim:

1. An electromagnetic exciter for use in acoustic signature inspection of the wheels of railroad cars comprising
   a. a base adapted to be secured in place adjacent the gage side of a railroad rail;
   b. an impact member comprising an impact head carried by a pivot arm;
   c. means mounting the pivot arm on the base for pivotal movement so that, when the exciter is in place, the head swings in a plane normal to the associated rail between an inactive position, wherein it is clear of passing wheels, and an active position, wherein it will strike the inner face of a passing wheel;
   d. yielding stop means defining said inactive position and serving to retard rebound of the impact member following return of that member to the inactive position;
   e. spring means biasing the impact member toward the inactive position;
   f. a solenoid mounted on the base and having a reciprocable armature which is spring biased to a rest position, and a coil which upon energization shifts the armature to an actuated position; and
   g. a lost motion force-transmitting connection between the armature and the pivot arm which affords to the impact member an initial range of motion wherein it is accelerated away from the inactive position by the armature as the latter moves from the rest to the actuated position, and a terminal range of motion wherein said member swings to its active position solely as a result of the kinetic energy imparted to it by the armature during said initial range of motion.

2. An exciter as defined in claim 1 wherein the impact member swings about a horizontal pivot axis.

3. An exciter as defined in claim 2 wherein the base has a portion which is designed to underlie and be attached to the base of a rail; the mounting means for the pivot arm includes adjustable connections to the base so that the position of the impact member relative to the rail may be adjusted; and the solenoid is attached to the base by adjustable connecting means so that the position of the solenoid relative to the impact member may be adjusted.

4. An exciter as defined in claim 1 wherein said impact head and force-transmitting connection are located at opposite sides of the pivot axis of the pivot arm.

5. An exciter as defined in claim 1 wherein the tangential velocity of the impact head when the latter reaches said active position is horizontally directed.

6. An exciter as defined in claim 1 including
   a. a DC power circuit containing the coil of the solenoid and a pair of SCRs whose anodes are connected to opposite ends of the coil, the first SCR being in series with the coil and the second SCR being in parallel with the coil;
   b. monostable multivibrator means responsive to receipt of an input signal for producing a positive control pulse of predetermined duration;
   c. means coupling the control pulse directly to the gate of the first SCR to thereby render the latter conductive upon production of the control pulse;
   d. inverting means coupling the control pulse to the gate of the second SCR to thereby render the latter conductive upon termination of the control pulse; and
   e. a capacitor connected between the anodes of the SCRs, the capacitor being charged in one direction through a path including the coil when the second SCR conducts and being charged in the opposite direction through a path containing a low value, high wattage resistor when the first SCR conducts,
   f. the charge developed on the capacitor during conduction by the first SCR serving to reverse the direction of current flow through that SCR and render it non-conductive when the second SCR becomes conductive, and vice versa.

7. Apparatus as defined in claim 6 in which the values of the components in the charging paths of the capacitor are so selected that the capacitor charges to the level required to effect said current reversal in a time period not greater than the duration of the control pulse.

8. Apparatus as defined in claim 6 including means for adjusting the duration of the control pulse; and means for varying the voltage applied to the coil.

9. Apparatus as defined in claim 6 wherein the circuit of the coil is free of arc-suppressing, shunting diodes; and which includes a voltage dependent resistor connected between the anode and cathode of each SCR, whereby the magnetic field of the coil can relax rapidly without imposing on the SCRs voltage spikes large enough to cause damage.

* * * * *